United States Patent [19]

Baumgärtner

[11] Patent Number: 5,123,286

[45] Date of Patent: Jun. 23, 1992

[54] ELECTRIC MEASURING DEVICE FOR MEASURING THE PROPAGATION DELAY OF AN ELECTRICAL SIGNAL

[75] Inventor: Manfred Baumgärtner, Fürth, Fed. Rep. of Germany

[73] Assignee: Siemens Aktiengesellschaft, Berlin & Munich, Fed. Rep. of Germany

[21] Appl. No.: 687,984

[22] Filed: Apr. 19, 1991

[30] Foreign Application Priority Data

Apr. 20, 1990 [EP] European Pat. Off. ...... 900107545.7

[51] Int. Cl.$^5$ .................. G01F 1/66; G01N 29/02
[52] U.S. Cl. .................. 73/861.27; 73/597; 364/569; 324/617
[58] Field of Search .............. 364/569; 73/597, 602, 73/609, 617, 861.27, 861.28; 324/617, 77 R

[56] References Cited

U.S. PATENT DOCUMENTS

| | | | |
|---|---|---|---|
| 4,334,431 | 6/1982 | Kohno | 73/597 |
| 4,372,163 | 2/1983 | Tittman | 73/597 |
| 4,483,202 | 11/1984 | Ogura | 73/861.27 |
| 4,541,279 | 9/1985 | Schomberg | 73/597 |
| 4,542,652 | 9/1985 | Reuter | 73/597 |
| 4,546,441 | 10/1985 | Burch | 324/617 |
| 4,603,589 | 8/1986 | Machida | 73/861.28 |
| 4,680,722 | 7/1987 | Tomasi | 364/569 |

FOREIGN PATENT DOCUMENTS 2853170 6/1980 Fed. Rep. of Germany.
WO88/02124 3/1988 PCT Int'l Appl..

OTHER PUBLICATIONS

Patent Abstracts of Japan, vol. 7, No. 231, Oct. 13, 1983; & JP-A-58120119 (Kansai Denriyoku) Jul. 16, 1983.

*Primary Examiner*—Kenneth A. Wieder
*Assistant Examiner*—Jose M. Solis
*Attorney, Agent, or Firm*—Kenyon & Kenyon

[57] ABSTRACT

To determine the exact instant ($T_s$) between the instant of transmission ($T_0$) of the leading-edge of a square-wave pulse ($S_1$) transmitted by a transmitter (4) and the instant ($T_1$) of the first appearance of the received signal ($S_2$), the latter is scanned with a threshold voltage (V) specifiable in steps, so that with n-time pulse transmission for repetition of the transmitting and receiving operation the threshold voltage is decreased by a value of $\Delta V$ in each transmitting and receiving operation. The instantaneous value of the threshold voltage (V) is compared with the peak values ($V_A$, $V_B$, $V_C$, $V_D$) of the amplitudes of the positive half-waves of the received signal ($S_2$). The instant at which the value of the threshold voltage (V) falls below the peak value ($V_A$, $V_B$, $V_C$, $V_D$) of the positive half-wave of the received signal ($S_2$) which follows each scanned half-wave is determined and the measurement of the propagation time delay for the positive half-wave is stopped at the following zero-crossover point ($T_A$ to $T_E$) of the received signal so that a group of threshold-voltage values (A, B, C, D) corresponds to each half wave of the received signal. From the maximum values of each group, the envelope (7) of the group of waves increasing in amplitude of the received signal ($S_2$) is formed and the point of intersection of the envelope with the baseline 0 of the group of waves of the received signal ($S_2$) is defined as the instant ($T_1$) of the first appearance of the received signal ($S_2$) in the receiver (5).

3 Claims, 2 Drawing Sheets

ELECTRIC MEASURING DEVICE FOR MEASURING THE PROPAGATION DELAY OF AN ELECTRICAL SIGNAL

BACKGROUND OF THE INVENTION

The invention relates generally to electronic measuring devices for measuring the propagation delay of an electrical, electromagnetic or acoustic signal between a transmitter and a receiver located at any distance from the transmitter, and more specifically to such a device where the signals delivered by the transmitter are square-wave pulses, and the signals reaching the receiver are groups of waves which increase in amplitude over several cycles and then decay, due to distortion of the pulses during the propagation, and whose period of vibration T is an integral multiple of the fundamental frequency of the transmitted pulses.

Measurements of the propagation delay between a transmitted and a received pulse signal can be made without an appreciable timing error only when the leading edge of the transmitted pulse arrives at the receiver at a definable instant. A prerequisite is that the pulse substantially retain its original shape during its propagation time so that the leading edge reaches the receiver with adequate steepness.

Frequently, however, this is not the case. For various reasons, either the transmitted pulse energy cannot be made large enough to exceed the trigger threshold set at the receiver, which must be well above the noise; or there are specific circumstances, as in the case of an ultrasonic measuring path for determining the flow rate of a medium, where the combined ultrasonic transmitter and receiver must transmit and receive the ultrasonic pulses through the wall of a tank. Since the tank may hold caustic media, such as acids or lyes, the tank is frequently made of high-grade steel several millimeters thick. In this case, the tank encloses the measuring path. The thickness of the wall of the tank and the length of the ultrasonic waves then are of about the same order of magnitude. A steel wall of this thickness will only be transparent to ultrasonic waves if its thickness is an integral multiple of one-half the ultrasonic wavelength in steel. However, the transmitted ultrasonic pulse, originally a square wave, will become so distorted in the transmission process that it arrives at the receiver, not as a pulse but as a group of waves that increases in amplitude over several cycles and then decays, and whose period of vibration is an integral multiple of the fundamental frequency of the transmitted pulse. The first appearance this wave train, which must be determined to measure the propagation time delay of the signal, gets obscured in the noise due to the amplitude and the small slope of the signal and the next vibration, and thus cannot be detected directly. Frequently, the voltage of the transmitted pulse cannot be simply increased in order to boost the received signal since in the case of many media the transmitting energy has to be kept low for safety reasons, e.g. in the petrochemical industry for explosion protection.

The present invention is directed to the problem of developing a method and device for determining the exact instant of the first appearance of a transmitted signal in applications where the transmitted pulse of an electrical, electromagnetic or acoustic nature arrives at the receiver as a group of waves that increases in amplitude and then decays, even when that instant is not distinguishable from the noise or then only with such small amplitude that the threshold is not measurable.

SUMMARY OF THE INVENTION

The present invention solves this problem by scanning a received signal ($S_2$) with a threshold voltage (V), which can be specified in steps. Then an instantaneous value of the threshold voltage (V) is compared with an amplitude of each positive half-wave of the received signal ($S_2$) and that instantaneous value of the threshold voltage is stored in a group of threshold voltage values corresponding to a particular positive half-wave if the particular positive half-wave exceeds the threshold voltage value. Next, propagation delays ($T_A$, $T_B$, $T_C$, $T_D$) for each positive half-wave, wherein each of said plurality of propagation delays are determined by defining the propagation delay for each positive half-wave to be a zero-crossing point following a point at which the amplitude of the positive half-wave falls below the instantaneous threshold voltage (V). This is repeated n times, decreasing the threshold voltage (V) by a value each time to determine a groups (A, B, C, D) of threshold voltage values, corresponding to the positive half-waves of the received signal ($S_2$). Next, a plurality of peak amplitude values ($V_A$, $V_B$, $V_C$, $V_D$) corresponding to a maximum value of the groups of threshold voltage values is determined. Finally, an envelope of the group of waves of the received signal ($S_2$) is formed from the peak amplitude values ($V_A$, $V_B$, $V_C$, $V_D$) and the propagation delays ($T_A$, $T_B$, $T_C$, $T_D$) of each positive half-wave, and a point of intersection of the envelope with a baseline 0 of the group of waves of the received signal ($S_2$) is determined. This point of intersection is defined as the instant ($T_1$) of a first appearance of the received signal ($S_2$) in the receiver and the propagation delay ($T_S$) of the received signal is determined from a difference between the instant of transmission ($T_0$) of a leading-edge of the square-wave pulse ($S_1$) and the instant ($T_1$) of the first appearance of the received signal ($S_2$).

This makes it possible to determine by the use of relatively simple electronic means, over a readily measurable range, voltage values on the basis of which the instant of the first appearance of the transmitted pulse in the receiver can be determined with a high degree of accuracy by means of a simple arithmetic operation.

DETAILED DESCRIPTION

Figure 1:
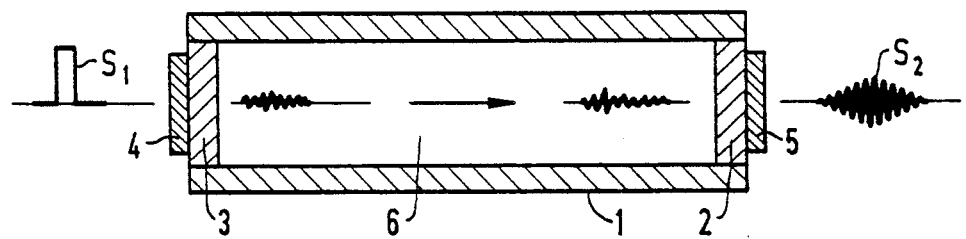
FIG. 1 is a diagrammatic representation of an ultrasonic measuring path for a liquid medium.

The embodiment shown in FIG. 1 is an ultrasonic measuring tube 1 with high-grade steel walls for containing caustic materials, such as acids or lyes. Mounted on the external surfaces of the two end walls 2 and 3 are transducers 4 and 5 that can be switched between TRANSMIT and RECEIVE. These transducers 4, 5 act through the end walls 2 and 3 on the medium 6 in such a way that the pulses transmitted by the transmitting ultrasonic transducer reach the receiving transducer directly or indirectly. The two ultrasonic transducers are alternately switched from TRANSMIT to RECEIVE, and the transmitted pulses therefore travel first through the medium in its direction of flow, indicated by the arrow, and then in the opposite direction. This results in different propagation delays of the ultrasonic pulse between transmitter and receiver, which are evaluated in a known manner, as described in German published patent application 35 39 971 and U.S. Pat. No. 3,329,017, for the purpose of determining the flow rate of the medium.

The two end walls 2 and 3 of the ultrasonic measuring tube 1, which are made of high-grade steel, are transparent to ultrasonic waves only if their thickness is an integral multiple of one-half the ultrasonic wavelength in steel. However, even when this sizing rule is observed, the received signal $S_2$ will deviate from the shape of the nearly rectangular transmitted pulse $S_1$ in that it no longer has any steep edges but consists of a group of waves that increases in amplitude over several cycles and then decays.

Figure 2:
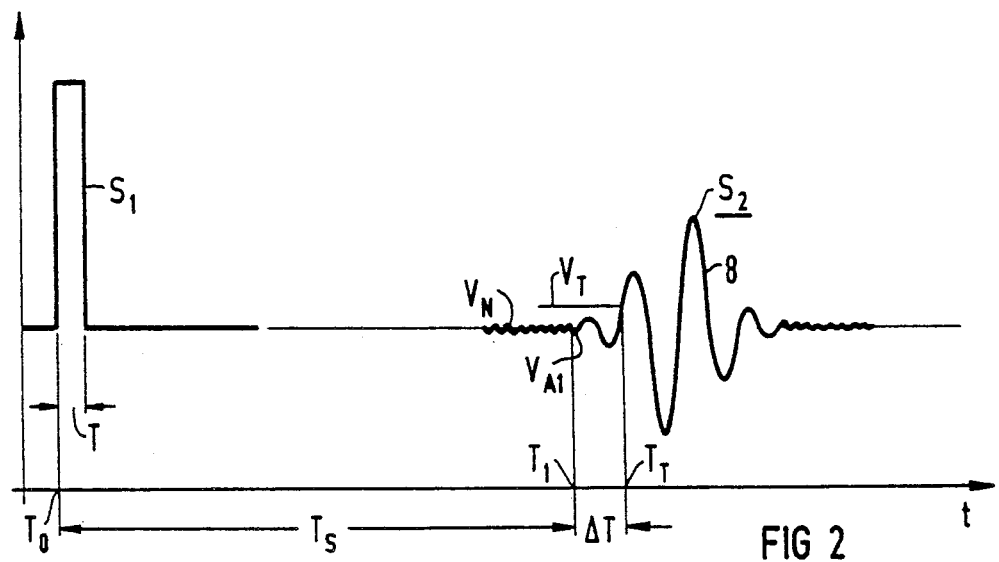
FIG. 2 is an amplitude-time graph of the transmitted and received signal.

FIG. 2 shows diagrammatically how the received signal differs from the transmitted signal. A transmitted pulse $S_1$ has a nearly rectangular form with edges that can be defined with respect to time, with the left edge as the starting edge marking the starting instant $T_0$. A first distortion of this pulse occurs already after passing through the first end wall of the transmitting transducer 4. The pulse assumes the form of a group of waves that increases in amplitude over several cycles and then decays. In traveling through the medium, this wave train has an increasing noise component $V_N$ superimposed on it. After passing through the second end wall of the ultrasonic measuring tube 1 associated with the receiving transducer 5, the received signal consists of a group of waves $S_2$ whose first vibration amplitude $V_{A1}$ is practically indistinguishable from the noise $V_N$ and therefore does not register in a threshold circuit. Now the start of this vibration $T_1$ marks the end of the propagation time of the transmitted pulse 7, and hence the true signal propagation delay $T_S = T_1 - T_0$. If a trigger threshold $V_T$ is established well above the noise amplitude $V_T$, a time factor of $\Delta T = T_T - T_1$ results.

Figure 3:
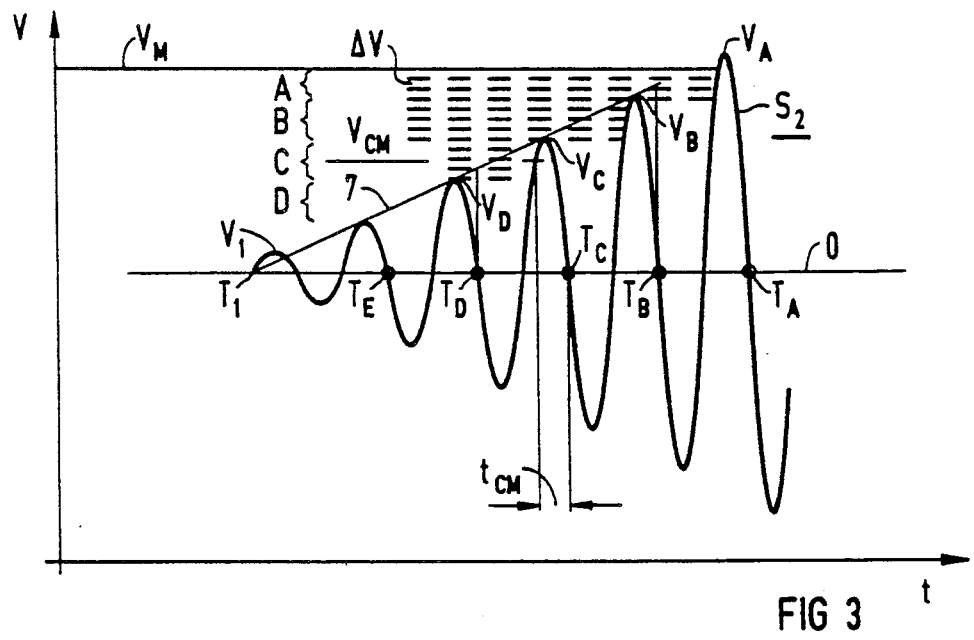
FIG. 3 shows an amplitude-time graph of the received signal and its recording for measurement purposes.

In accordance with the invention, the true signal propagation delay $T_S$ is determined indirectly, as will now be shown with reference to FIG. 3. In FIG. 3, the received signal $S_2$ is represented as a group of waves increasing in amplitude, its decaying portion having been omitted for the sake of simplicity along with the noise $V_N$. The received signal $S_2$ oscillates symmetrically about the vibration baseline 0. The zero-crossover points $T_A$ to $T_E$ of the individual full waves of the received signal $S_2$ are indicated on the time axis t. The spacing $T_N - T_{N-1}$ between two zero-crossover points is equal to the period of vibration T of the transmitted signal.

Now the amplitude peak values $V_A$ to $V_D$ of the received signal $S_2$ are determined by producing an irradiated ultrasonic pulse with threshold-voltage values V repeated n times which decrease by the value $\Delta V$ from pulse to pulse, beginning with a maximum value of $V_M$. Then the magnitude of the instantaneous threshold voltage is compared With the amplitude peak values $V_A$, $V_B$, $V_C$ and $V_D$ of the received signal, and whenever the peak value of an amplitude of the received signal exceeds the threshold voltage, the measurement of the propagation delay is stopped at the next zero-crossover point of the vibration at the instants $T_A$ to $T_D$. A polarity can thus be assigned to each individual vibration, and a group of threshold-voltage values A, B, C and D to its associated zero crossover. From the threshold voltages of the groups B and D, for example, that is, $V_B$ and $V_D$, and the propagation delays associated with these groups, there is then formed in a computing circuit an envelope 7 whose point of intersection with the vibration baseline 0 marks the instant $T_1$ as the instant of the first appearance of the transmitted pulse $S_1$ at the receiving ultrasonic transducer. The signal propagation time delay $T_S$ is then obtained by the formula $$T_S = T_B - (T_B - T_D)\left(\frac{V_B}{V_B - V_D}\right)$$ EQUATION 1 where
$T_B$ = propagation time delay of group B
$T_D$ = propagation time delay of group D
$V_B$ = maximum threshold value of group B
$V_D$ = maximum threshold value of group D In addition to the measurement of the propagation time delay of an ultrasonic pulse through a medium for determination of the speed of sound, for example, highly accurate measurement is also possible of the signal propagation delays $T_S$ in the direction of flow and counter to it, for the purpose of calculating the rate of flow in any medium with the aid of the differential propagation delay method mentioned at the outset. For this purpose, it will be advantageous to measure the propagation time delays of a fixed voltage of a specific group to the next signal zero-crossover point in the direction of flow of the medium 6, and counter to it, and to form the difference, instead of the signal propagation time delays extrapolated in the manner described above. To this end, the threshold voltages of group C, for example, are fixed at their mean value $V_{CM}$ and the propagation time delay $t_{CM}$ to the next zero-crossover point is measured in the direction of flow and counter to it. This approach offers the advantage that with varying total amplitudes of the received signal $S_2$ due to differential attenuation in the medium 6, the setting of the threshold to the mean value of group C can occur dynamically and in a self-correcting manner on the basis of the scanning of the received signal.

Figure 4:
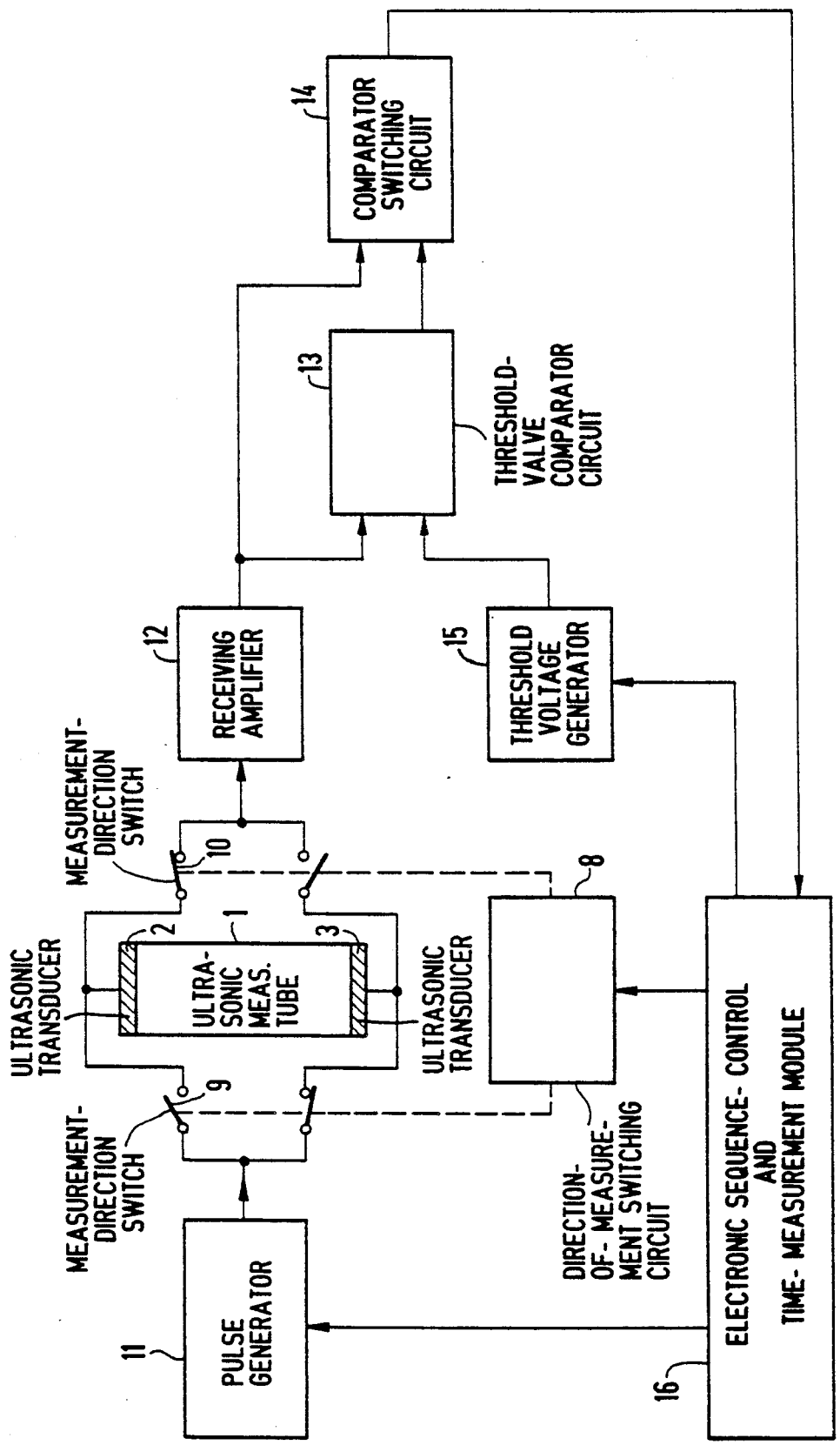
FIG. 4 is a block diagram of a measuring device having the characteristics of the present invention for the ultrasonic measurement of the rate of flow of liquid media.

As shown in FIG. 4, a measuring device for carrying out the measuring method described above consists of the ultrasonic measuring tube 1 with the ultrasonic transducers 2 and 3, which can be alternately switched from TRANSMIT to RECEIVE by means of a direction-of-measurement switching circuit 8. The transducer which is transmitting at a given time is connected by means of the measurement-direction switch 9 to a pulse generator 11 which produces the ultrasonic pulses. The transducer which is receiving at a given time is connected through the measurement-direction switch 10 to a receiving amplifier 12. The output of the latter is connected to a threshold-value comparator circuit 13 and to a comparator switching circuit 14. The second input of the threshold-value comparator circuit 13 is connected to a threshold-voltage generator 15, while the second input of the comparator switching circuit 14 is connected to the output of the threshold-value comparator circuit 13. An electronic sequence-control and time-measurement module 16 comprises a microcomputer which coordinates the measuring process and effects the time measurement on the basis of the pulses delivered by the comparator switching circuit 14 and of the threshold voltages $V_A$ to $V_D$ assigned to them.

What is claimed is:

1. A method for measuring a propagation delay of an electrical, electromagnetic or acoustic signal between a transmitter and a receiver located at any distance from the transmitter, wherein a transmitted signal delivered by the transmitter is a square-wave pulse, and a received signal reaching the receiver, as a result of distortion of the square-wave pulse during propagation, is a group of waves having positive half-waves which increase in amplitude over several cycles and then decay, and whose period of vibration T is an integral multiple of a fundamental frequency of the transmitted square-wave pulse, said method comprising the steps of:

a) transmitting the square-wave pulse ($S_1$) having an instant of transmission ($T_0$) of a leading edge;

b) scanning the received signal ($S_2$) with a threshold voltage (V) which is controlled in a plurality of steps;

c) comparing an instantaneous value of the threshold voltage (V) with an amplitude of each positive half-wave of the received signal ($S_2$);

d) storing the instantaneous value of the threshold voltage if the particular positive half-wave exceeds the threshold voltage value;

e) determining a plurality of propagation delays ($T_A$, $T_B$, $T_C$, $T_D$), wherein each of said plurality of propagation delays ($T_A$, $T_B$, $T_C$, $T_D$) corresponds to one of said plurality of positive half-waves, by defining the propagation delay for each positive half-wave to be a zero-crossing point following a point at which the amplitude of the positive half-wave falls below the instantaneous threshold voltage (V);

f) decreasing the threshold voltage (V) by a value $\Delta V$;

g) repeating steps a) through f) n times to determine a plurality of groups (A, B, C, D) of threshold voltage values, wherein each of said plurality of groups of threshold voltage values corresponds to one of the plurality of positive half-waves of the received signal ($S_2$); and h) determining a plurality of peak amplitude values ($V_A$, $V_B$, $V_C$, $V_D$), wherein each of said plurality of peak amplitude values corresponds to a maximum value of each of said plurality of groups of threshold voltage values;

i) forming an envelope of the group of waves of the received signal ($S_2$) from said plurality of peak amplitude values ($V_A$, $V_B$, $V_C$, $V_D$) and said plurality of propagation delays ($T_A$, $T_B$, $T_C$, $T_D$);

j) determining a point of intersection of the envelope with a baseline 0 of the group of waves of the received signal ($S_2$), said point of intersection being defined as the instant ($T_1$) of a first appearance of the received signal ($S_2$) in the receiver; and k) determining the propagation delay ($T_S$) of the received signal from a difference between the instant of transmission ($T_0$) of a leading-edge of the square-wave pulse ($S_1$) and the instant ($T_1$) of the first appearance of the received signal ($S_2$).

2. The method according to claim 1, further comprising measuring a plurality of signal propagation delays of a vibration selected from a fixed voltage of a specific group of threshold voltage values in a direction of flow of any medium and counter to the flow of the medium to calculate the flow rate of the medium.

3. An electronic measuring device for measuring a propagation delay of an electrical, electromagnetic or acoustic signal, said device comprising:

a) a transmitter transmitting a square-wave pulse n times;

b) a receiver located at any distance from the transmitter receiving a received signal ($S_2$), wherein said received signal as a result of a distortion of the square-wave pulse during propagation is a group of waves having positive half-waves which increase in amplitude over several cycles and then decay, and whose period of vibration T is an integral multiple of a fundamental frequency of the square-wave pulse;

c) a scanner scanning the received signal ($S_2$) with a threshold voltage (V) which is controlled in steps, said scanner decreasing the threshold voltage by a value $\Delta V$ in each transmitting and receiving operation;

d) a threshold-value comparator circuit comparing an instantaneous value of the threshold voltage (V) with a plurality of positive half-waves of the received signal ($S_2$) during each receiving operation to determine a plurality of peak values ($V_A$, $V_B$, $V_C$, $V_D$) corresponding to each of the plurality of positive half-waves of the received signal ($S_2$);

e) a threshold-value switching circuit;

f) a comparator circuit, in conjunction with said threshold-value switching circuit, stopping a measurement of a propagation delay of each positive half-wave ($T_A$, $T_B$, $T_C$, $T_D$) at a zero-crossing of the received signal ($S_2$), which follows an instant at which the positive half-wave falls below the threshold voltage, which follows each scanned half-wave;

g) a computing circuit measuring the propagation delay of the received signal by:

(i) forming an envelope of the group of waves of the received signal ($S_2$) from the plurality of peak amplitude values ($V_A$, $V_B$, $V_C$, $V_D$) and the propagation delay ($T_A$, $T_B$, $T_C$, $T_D$) of each positive half-wave;

(ii) determining a point of intersection of the envelope with a baseline O of the group of waves of the received signal ($S_2$), said point of intersection being defined as the instant ($T_1$) of a first appearance of the received signal ($S_2$) in the receiver; and (iii) determining the propagation delay ($T_S$) of the received signal from a difference between the instant of transmission ($T_O$) of a leading-edge of the square-wave pulse ($S_1$) and the instant ($T_1$) of the first appearance of the received signal ($S_2$).

* * * * *